(12) United States Patent
Hegarty (10) Patent No.: US 6,889,190 B2
(45) Date of Patent: May 3, 2005

(54) HAND HELD MEDICAL PRESCRIPTION TRANSCRIBER AND PRINTER UNIT

(75) Inventor: David D. Hegarty, Lee's Summit, MO (US)

(73) Assignee: Rodan Enterprises, LLC, Lee's Summit, MO (US)

( * ) Notice: Subject to any disclaimer, the term of this patent is extended or adjusted under 35 U.S.C. 154(b) by 625 days.

(21) Appl. No.: 09/770,087

(22) Filed: Jan. 25, 2001

(65) Prior Publication Data

US 2002/0099534 A1 Jul. 25, 2002

(51) Int. Cl.$^7$ ............................................. G10L 21/06
(52) U.S. Cl. ........................... 704/275; 704/270; 705/2; 705/3
(58) Field of Search .............................. 704/270, 270.1, 704/275; 705/2, 3

(56) References Cited

U.S. PATENT DOCUMENTS

| | | | |
|---|---|---|---|
| 4,392,409 A | | 7/1983 | Coad, Jr. et al. |
| 4,435,617 A | | 3/1984 | Griggs |
| 5,390,281 A | * | 2/1995 | Luciw et al. ................. 706/11 |
| 5,655,136 A | * | 8/1997 | Morgan ....................... 382/187 |
| 5,729,694 A | | 3/1998 | Holzrichter et al. |
| 5,737,539 A | | 4/1998 | Edelson et al. |
| 5,749,072 A | * | 5/1998 | Mazurkiewicz et al. ..... 704/275 |
| 5,812,882 A | | 9/1998 | Riji et al. |
| 5,845,255 A | | 12/1998 | Mayaud |
| 6,178,403 B1 | * | 1/2001 | Detlef ......................... 704/270 |
| 6,292,783 B1 | * | 9/2001 | Rohler et al. .................. 705/2 |
| 6,434,403 B1 | * | 8/2002 | Ausems et al. ........... 455/556.2 |
| 6,463,413 B1 | * | 10/2002 | Applebaum et al. ........ 704/256 |
| 6,691,158 B1 | * | 2/2004 | Douvikas et al. ........... 709/219 |

\* cited by examiner

*Primary Examiner*—Susan McFadden
(74) *Attorney, Agent, or Firm*—Hovey Williams LLP (57) ABSTRACT

This invention relates to a unitary hand held medical prescription transcriber and printing unit. More specifically, a small, portable electronic device is provided which can record words spoken by a physician and from those words generate a printed medical prescription that is delivered directly from the device itself. The unit digitizes words spoken by the user, processes the speech to recognize the words spoken by comparing the acoustic spectral characteristics of the spoken words to the characteristics of a database of known words, formats those words in the form of a prescription, and prints the prescription onto paper using a small integral printer contained in the unit. In a alternate embodiment, the unit may display the prescription on a liquid crystal display screen and the user may edit the prescription before printing a hard copy. The unit assists in accurate dispensing of medicines by providing a legible prescription printout, while at the same time being neither time consuming nor difficult to operate.

29 Claims, 9 Drawing Sheets

HAND HELD MEDICAL PRESCRIPTION TRANSCRIBER AND PRINTER UNIT

FIELD OF THE INVENTION

This invention relates to voice transcribing and print out of the transcribed message, and particularly to an integrated, hand held transcriber and printer unit especially adapted to permit a physician to dictate a medical prescription into the unit and that will print out a hard copy of the prescription while the unit is held in the doctor's hand.

BACKGROUND OF THE INVENTION

Potentially serious and untoward medical problems can occur when a pharmacist inadvertently dispenses a wrong drug because of inability to read what is often virtually illegible handwritten medical prescriptions. The present invention provides an alternative way to create accurate and legible medical prescriptions to ensure that drugs are dispensed as prescribed. This greatly benefits pharmacists and patients alike. Computerized medical prescription creation and management systems have been proposed in the past, but these systems have not found wide-spread acceptance because they have been time consuming and often required input into multiple computers or transfer of data into other computers before the prescription was complete. In view of the fact that time constraints are of importance to medical personnel, this invention serves to make the prescription completion process as quick and efficient as possible through the use of a hand held, self-contained device.

The invention applies speech recognition software to convert the voice input of the medical personnel into a printed prescription. Voice and sound recognition devices are disclosed in: U.S. Pat. No. 5,812,882 issued Sep. 22, 1998; U.S. Pat. No. 5,729,694 issued Mar. 17, 1998; U.S. Pat. No. 4,435,617 issued Mar. 6, 1984; and U.S. Pat. No. 4,392,409 issued Jul. 12, 1983. Prior prescription creation and management systems are described in patent Nos.: U.S. Pat. No. 5,845,255 issued Dec. 1, 1998; and U.S. Pat. No. 5,737,539 issued Apr. 7, 1998.

SUMMARY OF THE INVENTION

This invention concerns a hand held medical prescription transcriber and printer as an integrated unit. The transcriber records the words spoken by the user and then utilizes speech recognition software to convert the recorded sound into text. The device then formats the text for printing and prints it out as a hard copy on paper. The device is entirely self-contained because it incorporates an internal power supply and printer in the hand held unit. These features contribute to the simplicity and ease of operation, as well as the speed at which it functions.

In a preferred embodiment, the prescription transcriber and printer unit includes a voice responsive input device which converts the user's spoken word acoustic inputs into analog signals. A converter converts the analog signals into corresponding outputted digital signals. A database of medical prescription information is provided which stores a library of drugs and dosage regimes in digital format. A combination of digital signal and digital data matching code segments define a program which is operable to match outputted digital signals from the converter with corresponding digital data stored in the database. Additional code segments present components for retrieving the digital data stored in the database which matches the digital signals outputted from the converter and also serve to format the retrieved digital data from the database into a form representative of a medical prescription and dosage instructions. A printer incorporated into the unit receives the formatted digital prescription drug and dosage instruction data and prints out the prescription information as readable hard copy that can be handed to the patient at the time of prescribing of a drug.

In one form of the invention, the device is very simple, with only one "record" button which the user employs to start and stop the voice recording. Upon completion of recording, the device automatically processes the spoken words and prints the prescription as hard copy. In another form, the unit includes a voice activated input device, along with a small liquid crystal display screen on which the prescribed drug including dosage information is displayed prior to print out of the prescription. This form may if desired also include a manually manipulable dial which the user employs to scroll through a list of drugs contained in the language database in order to correct mistakes which might occur during the speech recognition process, or to select an alternate drug with similar therapeutic properties.

A still further form of the invention provides for electronic communication between the hand held device and another stand alone computer, thereby permitting the user to update the database of drugs and/or dosing instructions as, for example by accessing an updated list stored on the remote computer and then downloading that list onto the hand held medical prescription transcriber.

Data storage means may be provided in the hand held transcriber and printer unit which serves to store the data representative of each prescription and dosage information as it is written as a history of prescriptions prescribed over a pre-determined period of time, thereby permitting that historical information to be downloaded to a separate data storage site.

Although speech recognition software may be incorporated in the prescription transcriber and printer unit which recognizes and processes more complex information than a list of drugs and dosage instructions therefor, such as the patient's name and address, in most instances it is simpler for the physician to write the patient's name on the hard copy print out after the prescription is printed and delivered from the hand held unit. The principle purpose of the present invention is to avoid mistakes by a pharmacist who is unable to read the doctor's drug and dosage instructions thereby causing a prescription filling error. This problem normally does not occur in connection with patient's name and address because that information can be provided by the patient and verified by the pharmacist at the time the prescription is presented for filling by the pharmacist.

DETAILED DESCRIPTION

I. Preferred Embodiment

Figure 1:
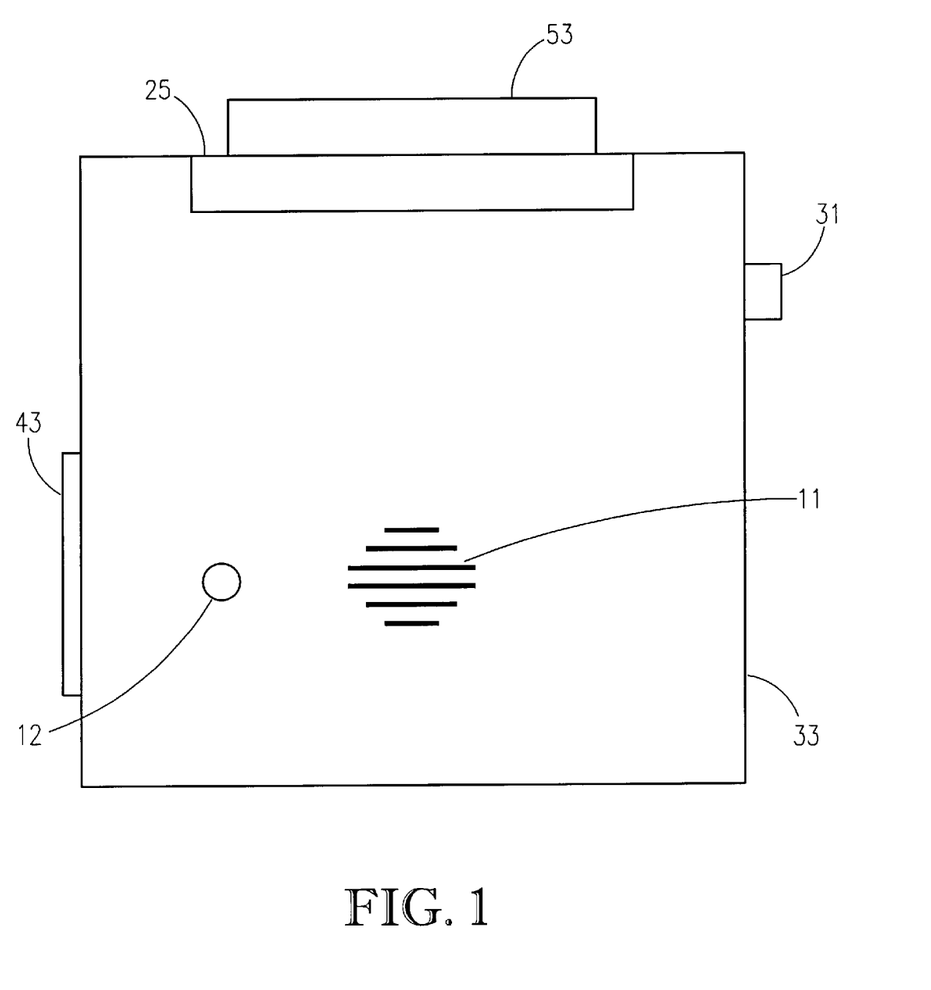
FIG. 1 shows an external representation of the invention in its preferred embodiment.

FIG. 1 depicts an external representation of a hand held medical prescription transcriber and printer unit 10 in its preferred embodiment and that contains all of the components that are necessary for the most useful and efficient operation of the device. Externally, the only features of the unit 10 visible to the user are the case 12, the microphone 14, the light-emitting diode (LED) 16, the manually operable controller 18, the long-term storage (Flash Memory Card) 20, the printer 22, and the paper 24 which is discharged from printer 22. The simplicity of the preferred embodiment of the invention assures compactness of the unit and maintains the efficiency of the device for the user.

Figure 2:
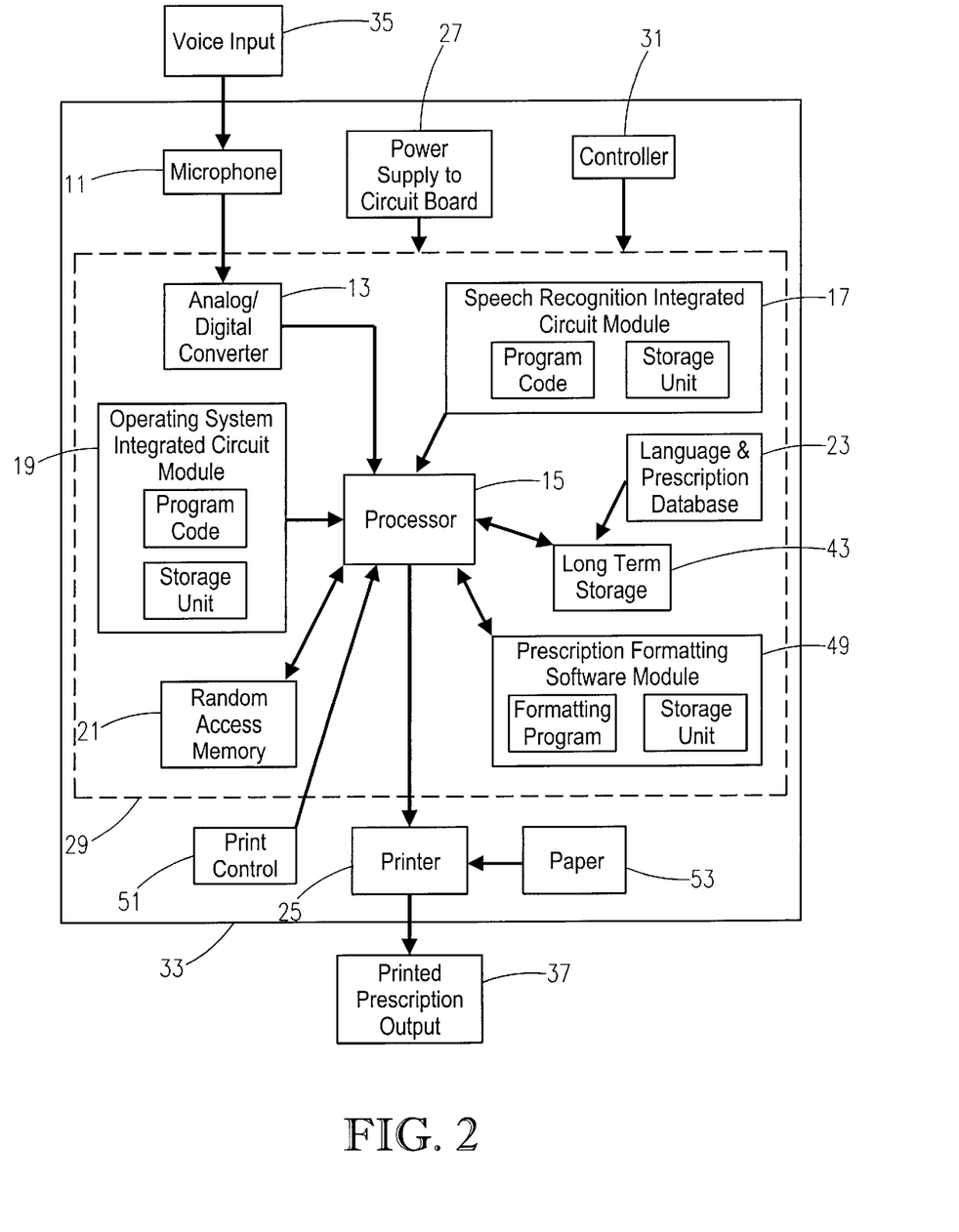
FIG. 2 is a simplified block diagram showing the components of one embodiment of the invention.

FIG. 2 is a block diagram showing the internal arrangement of the components of the embodiment of FIG. 1. Unit 10 internally contains a power supply 26 connected to an associated circuit board 28. The case 12 is desirably formed from a synthetic resin material to present standard, injection-molded plastic "clam shell" construction, or alternatively, fabricated utilizing conventional manufacturing techniques and materials to provide a suitable impact-resistant and sturdy housing for the internal components. Case 12 is constructed of a size and shape to ergonomically permit the user to hold and operate unit 10 while held with one hand.

Case 12 has appropriate internal attachments such as screw holes or pockets, for mounting the internal components of unit 10, including the power supply and circuit board 28, as well as an internally mounted printer 22, a supply roll of thermal paper 24 in the printer, a microphone 14, and an On-Off switch 18 functioning as a controller for operation of the unit 10. Case 12 is provided with openings in the wall structure thereof in a position allowing for voice sound waves created by the physician's voice during operation of unit 10 to reach and be sensed by the microphone 14. An On-Off LED indicator 16 is mounted on the case 12 in disposition to permit ready viewing thereof when the unit 10 is held in its operating position by a physician. A suitable slot is provided in a sidewall of case 12 to permit ejection of paper 24 from the roll thereof. Another slot in a sidewall of unit 10 allows a storage device such as a Flash Memory Card 20 to readily be inserted and removed from the case 12. A normally closed battery compartment has a removable or swingable closure permitting insertion and replacement of the batteries making up a part of power supply 26.

Power supply 26 consists of a battery or an adequate number of batteries to provide required voltage and current to operate the electrical and mechanical components of unit 10. In addition, voltage and current regulating hardware is incorporated in the power supply to assure that correct voltage or voltages and currents are continuously supplied to the various electrical and electronic hardware components forming a part of the prescription transcriber unit 10. The power supply 26 may consist of a power supply system consisting of rechargeable batteries (e.g., lithium ion batteries), an integrated battery recharger powered by external DC power input, an appropriate input for the DC power, and the associated voltage and current regulating hardware required to deliver the correct voltage or voltages and currents.

Microphone 14 may be a standard device of the type that is operable to convert the acoustic inputs created by the user's voice into analog electrical signals during use of unit 10. The acoustic inputs are represented diagrammatically in FIG. 2 by the function block 30 of FIG. 2.

The microphone 14 is preferably powered by the power supply 26. In the preferred embodiment, controller 18 represents a simple single pole single throw switch (i.e., on/off) having a finger operable switch operator normally biased toward the open position of the switch. Depressing the switch operator against the spring bias thereon effects closing of the switch contacts, while letting up on the operator results in opening of the switch contacts.

Alternatively, the controller 18 may be in the form of voice-activated switch which closes upon receipt of a close-range acoustic input by a physician speaking into the microphone 14. Desirably, the voice-activated switch is of the type which responds to sound emanating in close proximity to the device, such as a person speaking directly into the device, but that does not respond to distant noise, such as conversations elsewhere in the same room. A voice-activated switch normally is practical only in relatively well controlled and quiet environments, without a lot of background noise. A desirable low noise environment is usually present in physician's offices and in hospitals.

The circuit board 28 contains all of the electronics and programs required for operating the handheld medical prescription transcriber, including the analog-to-digital converter (A/D) 32, the central microprocessor unit 34, the operating system module 36, the speech recognition integrated circuit module 38, the prescription formatting software module 40, the language and prescription database 42, the removable long-term data storage card 20, and random access memory (RAM) chip 44. The circuit board 28 is of standard construction consisting of laminations of plastic and copper etched to provide proper electrical circuit connections between the various electronic components which are attached to the circuit board 28.

The circuit board 28 and all the components attached thereto are powered by the power supply 26. The A/D converter 32 converts the analog signal produced by the microphone 14 into a digital signal which can be sampled by the central microprocessor unit (CPU) 34. The CPU may be a standard microprocessor such as those typically used for notebook computers. However, the CPU must be relatively fast in order to efficiently process the speech recognition programs. A practical implementation of the device utilizes for example a notebook Pentium III processor manufactured by Intel, ranging from the 600 MHZ up to the 850 MHZ chip.

The CPU 34 processes the digitized voice input it receives from the A/D converter 32 by utilizing instructions and data contained in the operating system module 36, the speech recognition module 38, the prescription formatting module 40, and the language and prescription database 42. The language and prescription database 42 desirably contains all the words and speech recognition data (i.e., acoustical statistics) required by the speech recognition module 38 and prescription formatting module 40 to operate properly. The digital information contained in database 42 is stored in the long-term storage memory card 20.

The information contained in database 42 stored in card 20 may be limited to a subset of the English language plus all the drugs contained in such standard references as the Physicians Desk Reference. The limited subset of English consists of only words necessary for dispensing prescriptions, including numbers, and words associated with dosages (e.g., "milligram", "tablets", etc.), frequency (e.g., "per day"), duration (e.g., "for seven days"), and administration instructions (e.g., "by mouth"). This constitutes only a few thousand words, as opposed to in excess of at least one hundred thousand words required for a competent spoken English recognition system. The limited amount of words and numbers that must be stored and made accessible, significantly decreases the amount of actual information that must be stored in the database card 20.

Furthermore, the digital data stored in database 42 can be arranged by conventional software into categories in order to assist the prescription formatting module 40 in converting the spoken words into a prescription format 40. In view of the fact that some words may be included in more than one category, in addition to all the words, the database should also store characteristic acoustical statistical information about each word. This information in digital format is required by the speech recognition module 38 in order to efficiently convert the digitized spoken words into text.

The long-term data storage card 20 desirably is a rewritable long-term electronic storage media such as a Compact Flash Memory Card which can be easily removed and replaced or reprogrammed for frequent updating. Since new drugs are frequently and constantly being introduced to the market, the database must be easily updated. A Flash Memory Card is preferred for this application. These are widely available from many suppliers. A 64 MB Apacer ATA Flash Memory Card is adequate in most instances. This card is in the PCMCIA format and is of a type that is accessible from the outside of the transcriber and can be removed and replaced by another card provided by a supplier and containing an updated database of drugs. Alternatively, the user can update the contents of the Flash Memory Card 20 by putting it in a separate device attached to a personal computer.

The operating system module 36 contains all the instructions (i.e., programs) required by the device to operate properly. The operation of transcriber and printer unit 10 can best be understood from the diagrammatic flow chart of FIG. 3. The OS module 36 consists of the operating system program code 46 and an appropriate storage unit 48 for this code. The operating system module 36 preferably provided as a "firmware" module wherein the program code 46 is hardwired or "burned" into an integrated circuit (i.e., a chip) as the storage module 48. The use of an integrated circuit chip such as a Programmable Read Only Memory module 48 (PROM) ensures the most rapid loading and processing of operating system commands by the CPU 34. Since the speed of operation of unit 10 is essential to its convenience, rapid loading and processing of data is desirable. PROM's are widely available in a variety of capacities and from a variety of vendors. The IC chip can either be hardwired to circuit board 28 or it can be installed into a socket attached to the circuit board such that it can be replaced in order to upgrade the operating system. As an alternative arrangement, the storage unit 48 may comprise a small part of the long-term storage 20. This allows the operating system to be periodically updated.

The speech recognition module 38 contains all of the instructions (i.e., programs) required by the unit 10 to process the words spoken by the physician and received by the microphone 14 which are then converted into written text. The speech recognition module 38 consists of the speech recognition program code 50 and an appropriate storage unit 52 for this code. This module 38 may be in the form of a "firmware" module wherein the program code 50 is hardwired into an integrated circuit chip which also serves as the storage module 52. The use of an integrated circuit chip as module 38 again ensures the most rapid loading and processing of speech recognition commands by the CPU 34. Since the speed of operation of this device is essential to its convenience, such rapid loading and processing is desirable. The IC chip 38 can be hardwired to the circuit board 28 or it can be installed in a socket attached to the circuit board such that it can be replaced in order to upgrade the speech recognition software. As a farther alternative, the storage unit 52 could represent a part of the long-term storage device 20, thus allowing the speech recognition software to be upgraded periodically in the same manner as the prescription database 42, as described above.

The prescription formatting module 40 contains all of the instructions (i.e., programs) required by the device to format the text produced by the speech recognition program into a form representative of a medical prescription and which can be printed by the printer. The prescription formatting module 40 consists of the prescription formatting program code 54 and an appropriate storage unit 56 for this code. This module 40 may also be provided as a "firmware" module in which the formatting program code 54 and the storage unit 56 are both hardwired into an integrated circuit chip. The IC chip can be hardwired to the circuit board 28 or it can be installed in a socket attached to the circuit board such that it could be replaced in order to upgrade the formatting module 40. The storage unit 56 could if desired be a part of long-term storage unit 20, thus allowing periodic upgrading of the formatting program.

Random Access Memory (RAM) 44 is required by the CPU 34 in order to temporarily store data, such as the digitized speech, and the program instructions. In order to properly run the speech recognition programs, at least 32 MB of RAM and preferably 64 MB of RAM is required. Standard RAM can be used. For the most practical and compact implementation of unit 10, 64 MB of SDRAM in one 72-pin DIMM may be utilized.

The printer 22 creates an easily readable printout of the medical prescription 58 (FIG. 2). The printer must be compact enough so that it can easily fit in a hand held device. Such printers are now in widespread use in a variety of compact, portable electronic devices. The printer 22 that is used for the preferred embodiment of this invention is the Densitron DPTH 804 Thermal OEM Printer. This thermal print head printer 22 has the ability to print bar codes, text, and graphics and is very capable for use in mobile, handheld devices due to its compact size. The printer 22 includes a high performance processor, battery, and print mechanism.

The paper source 24 can be a roll of standard thermal paper appropriate for use by the printer 22. The user can employ if desired thermal paper with preprinted prescription forms including the doctor's name, medical identification number, and other desired information.

The long-term storage 20 included in the preferred embodiment also provides for the recording of a number of prescriptions for future printing, or for input into a patient's records. The entering of the prescriptions into the long-term storage 20 is automatic and occurs simultaneously with printer. The device's CPU 34 writes the prescription data directly to the long-term storage card 20. The stored prescription records can be downloaded to a personal computer later by removing the Flash Memory Card 20 from the transcriber and reading it with a separate device attached to the personal computer. The long-term storage 20 also provides for downloading customized prescription forms into the transcriber. Again, using a separate device attached to a personal computer, the user can save electronic forms on the Flash Memory Card 20 to be used by the operating system when printing the prescription. In this manner, various customized information can be automatically printed on the prescription.

II. Operating System Software Flow of Unit 10

Figure 3:
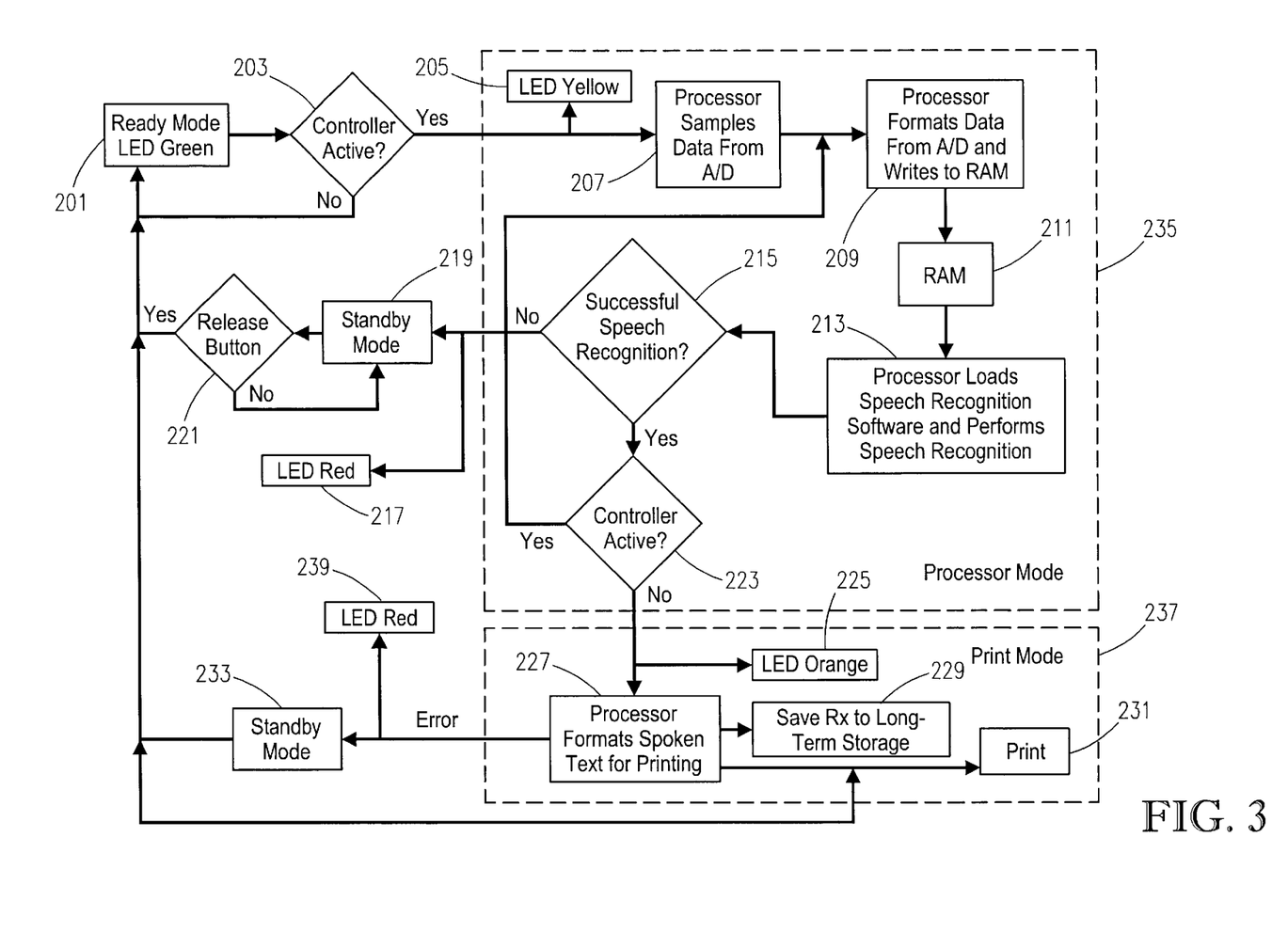
FIG. 3 is a software or firmware block diagram setting forth central processor activity during the flow of the operating system for the device in the embodiment of FIG. 2.

The overall software flow function of the medical prescription transcriber and printer unit 10 that is implemented via the operating system module 36 for the preferred embodiment of the device is shown diagrammatically in FIG. 3. In the preferred, simplest embodiment of the unit 10, the device has four modes: Ready Mode 100, Processor Mode 102, Standby Mode 104, and Print Mode 106, with activation of the unit being controlled by movement of the manual control switch 18.

Prior to activation of the voice recording controller function 108 by actuation of switch 18 as shown diagrammatically in FIG. 3, the device remains in ready mode 100, a passive state. The ready mode state 100 of unit 10 is indicated by illumination of the green LED as shown in the flow chart of FIG. 3.

Upon pressing of the manually operable control switch 18 to render the controller function 108 active, the device moves into processor mode 102. Shifting of the operative condition of unit 10 from ready or standby mode 100 to processor mode 102 is indicated to the user by changing of the color of the LED to yellow 110. In processor mode 102, the CPU begins to sample the analog to digital signals from analog/digital converter 32 at a specified sample rate indicated by processor function block 112 of FIG. 3. In a preferred implementation of this invention, a sample rate of approximately 10,000 times per second is used. The processor 34 formats the digital signals received from the A/D converter 32 and writes the formatted data to RAM 44 as indicated by function block 114 of FIG. 3. When approximately 10 milliseconds of data have been recorded to RAM 44, the processor 34 also loads the speech recognition software from the speech recognition integrated circuit chip 38 and begins to perform the speech recognition algorithm as indicated by function block 116 of FIG. 3.

As long as the speech recognition process proceeds smoothly as indicated by function block 118, the controller 108 remains active as indicated by function block 120, the processor 34 continues to sample the digital signals from A/D converter 32 and continues to write data to RAM 44. If at any time the speech recognition software submits an error message as output, the processor 34 will stop sampling the A/D and the unit 10 will enter Standby Mode 104. The color of the LED will change to red as indicated by function block 122, as an indication to the user that an error in processing has occurred.

When the manually manipulable switch 18 is released to deactivate controller function 108, the device will return to Ready Mode 100. The color of the LED will return to green, as an indication to the user that the device is ready to start recording again. The only reason that the processor 34 would send such an error message is because a word spoken by the user could not be recognized as being in the database of module 38. This is not a likely occurrence given the relatively small size of the database of words required for the medical prescription transcriber.

If the speech recognition process proceeds without submitting an error message, the processor 34 will continue to sample the output from A/D converter as indicated by function block 112 and to write data to RAM 44 until the user releases the switch 18 causing the speech recording controller function 120 to cease operation. Upon release of the controller active function as indicated by function block 120, the unit 10 moves into Print Mode 106. Print Mode 106 is indicated to the user by changing of the color of the LED to orange as represented by function block 122. In Print Mode 106, the processor 34 loads the prescription database information from card 20 and formatting software from module 40 and formats spoken text which has been matched with drug, dosing instructions, and other stored data from the prescription, dosing instruction and other word database from the prescription and language database for printing out on printer 22.

If the spoken text cannot be properly processed for printing as a prescription, an error message will be sent by the prescription formatting software. The processor will stop the A/D sampling function 112 and the device will enter Standby Mode 124. The color of the LED will change to red as represented by function block 126, as a sign to the user that an error in processing has occurred. After a brief (e.g., 2 or 3 second) pause, the device will return to Ready Mode 100.

Once the text has been processed as indicated by function block 128, the formatted data, including any previously downloaded customized forms, will be submitted to the print driver, which will in turn send it to the printer 22, which will print out prescription as represented by function block 130 of FIG. 3. This completes the cycle, and the device is returned to ready mode 100.

III. Speech Recognition System

Figure 4:
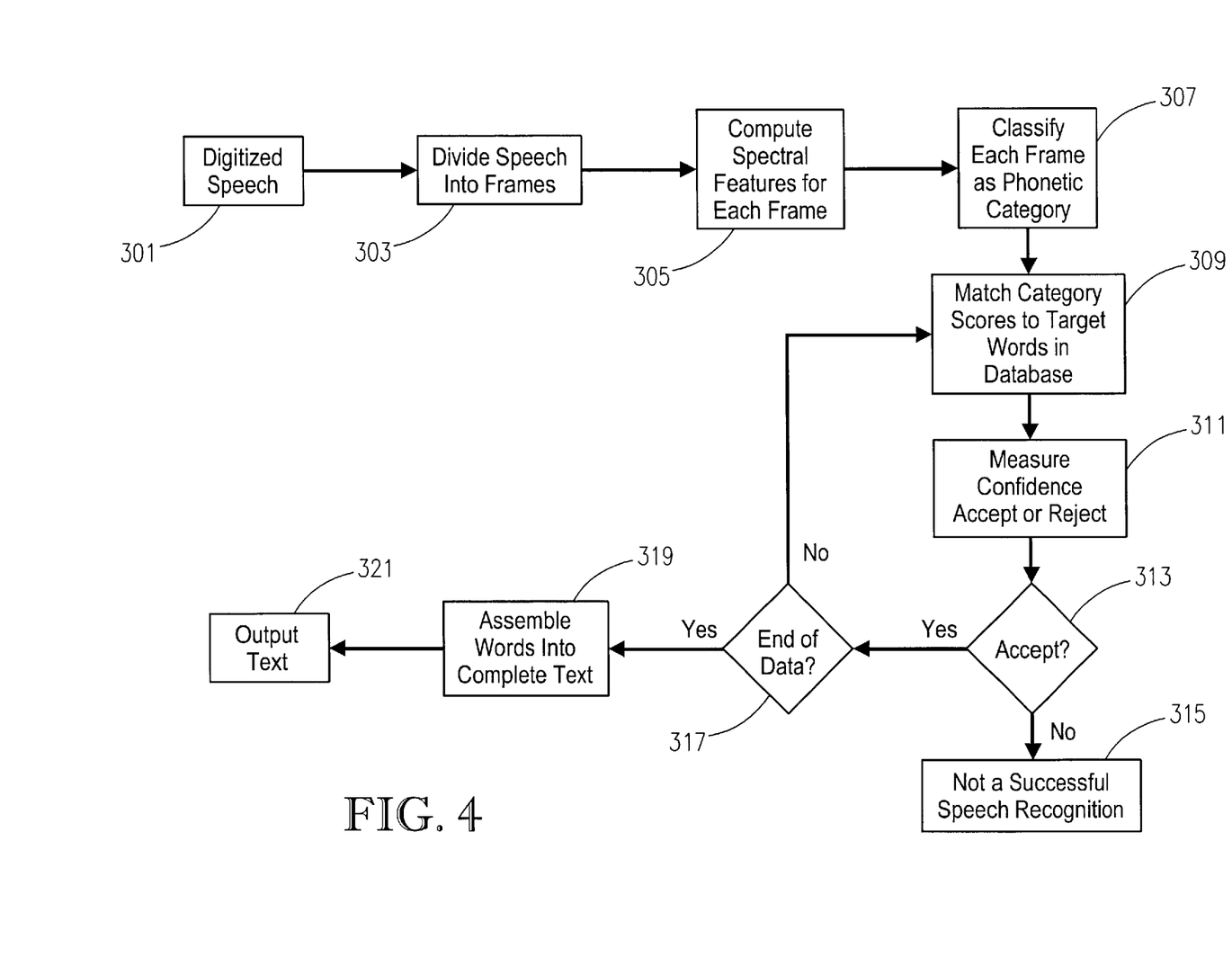
FIG. 4 is a software or firmware block diagram setting forth the flow functions of the speech recognition program.

FIG. 4 illustrates the software flow function of the speech recognition module 38. The processor 34 which calls the speech recognition program from module 38 directs digitized speech, identified by function block 200, into RAM 44 for storage. The processor 34 divides this speech into separate pieces as indicated by function block 202 with each frame or piece being approximately 10 milliseconds in length. Each of these pieces is a frame. For each frame of speech, the speech recognition software conducts a complex spectral analysis and computes several spectral features identified by function block 204 of the FIG. 4 flow chart. In a preferred embodiment, these spectral features include twelve mel-frequency cepstral coefficients (MFCC), twelve coefficients indicating the degree of change of the MFCCs, one energy feature, and one feature indicating the degree of change of energy. Such spectral analysis is carried out in accordance with standard techniques.

Once the spectral features for a given frame are calculated, the values for those features are classified as to phonetic category as indicated by function block 206, and then compared to values for those features for the various phonemes and subphonemes in the language database 42, as indicated by function block 208.

Phonemes are the simplest elements of spoken language. For example, in English, the sound "ee" is a phoneme. There are a finite number of phonemes in each language. However, the spectral characteristics of each phoneme can vary depending upon the placement of that phoneme relative to other phonemes in spoken language. Therefore, it is often necessary to consider subphonemes which comprise an entire phoneme.

Because the spectral features of a given phoneme or subphoneme will vary depending upon who is saying the word, it is often not possible to definitely determine which subphoneme a certain frame represents. Instead, a probability is assigned to the association of the frame with given phonemes. For example, if a speaker says the drug name "Xanax", the first phoneme is the sound "Z". Depending upon how it is said, the software may determine a high probability (e.g., 85%) that this frame represents the sound "Z" and a lesser probability (e.g., 15%) that it represents the sound "S". In this manner each frame is classified.

The phoneme and subphoneme classifications of each frame are then assembled, and those series are compared to the series of phonemes associated with the various words in the language database. Since each frame is associated with several phoneme matches with varying probabilities, a series of frames corresponds to a number of potential combinations of those subphonemes and phonemes with varying probabilities. Those combinations are compared to the combinations for words in the language database 42, and using this process, the software can determine the probability that the speaker spoke one of several target words.

In a very large language database, such as the entire English language, there are often many possible target words, and depending upon the clarity with which the speaker says his words, the probabilities associated with several target words may be nearly equal. This makes speech recognition challenging. In the present invention, however, the language database 42 is significantly smaller than the entire English language. This assures an almost 100% certainty of a correct match being made of written text to spoken text.

Once a match for a given word is made, the probability (confidence) associated with that word is examined as indicated by the measure of confidence function block 210. If the probability exceeds a specified threshold (e.g., 80%), the word will be accepted as indicated by function block 212. If the probabilities associated with all target words fall below the threshold, but if the probability associated with one of the words is significantly higher than that associated with the next best choice, the word is accepted. If the probabilities associated with all target words are small and similar, then all words are rejected and the system has not successfully recognized the spoken words. This will occur if (1) the speaker says words not in the database, (2) the speaker speaks very poorly (e.g., mumbles, coughs, etc.), or (3) the spoken words are mixed with significant background noise. The first case should not occur so long as the database of drugs is regularly updated, and the other two cases are easily avoided by the user.

Once a successful match is made as indicated by function block 212, the speech recognition software will continue to process the digitized speech until it has processed all of the data submitted for analysis as indicated by function block 214. The various word matches will then be assembled into the complete text spoken by the user. This text is then stored in RAM 44 as indicated by function block 216 and outputted as text pursuant to function block 218 to be processed for display, editing, or printing.

IV. Prescription Formatting

Figure 5:
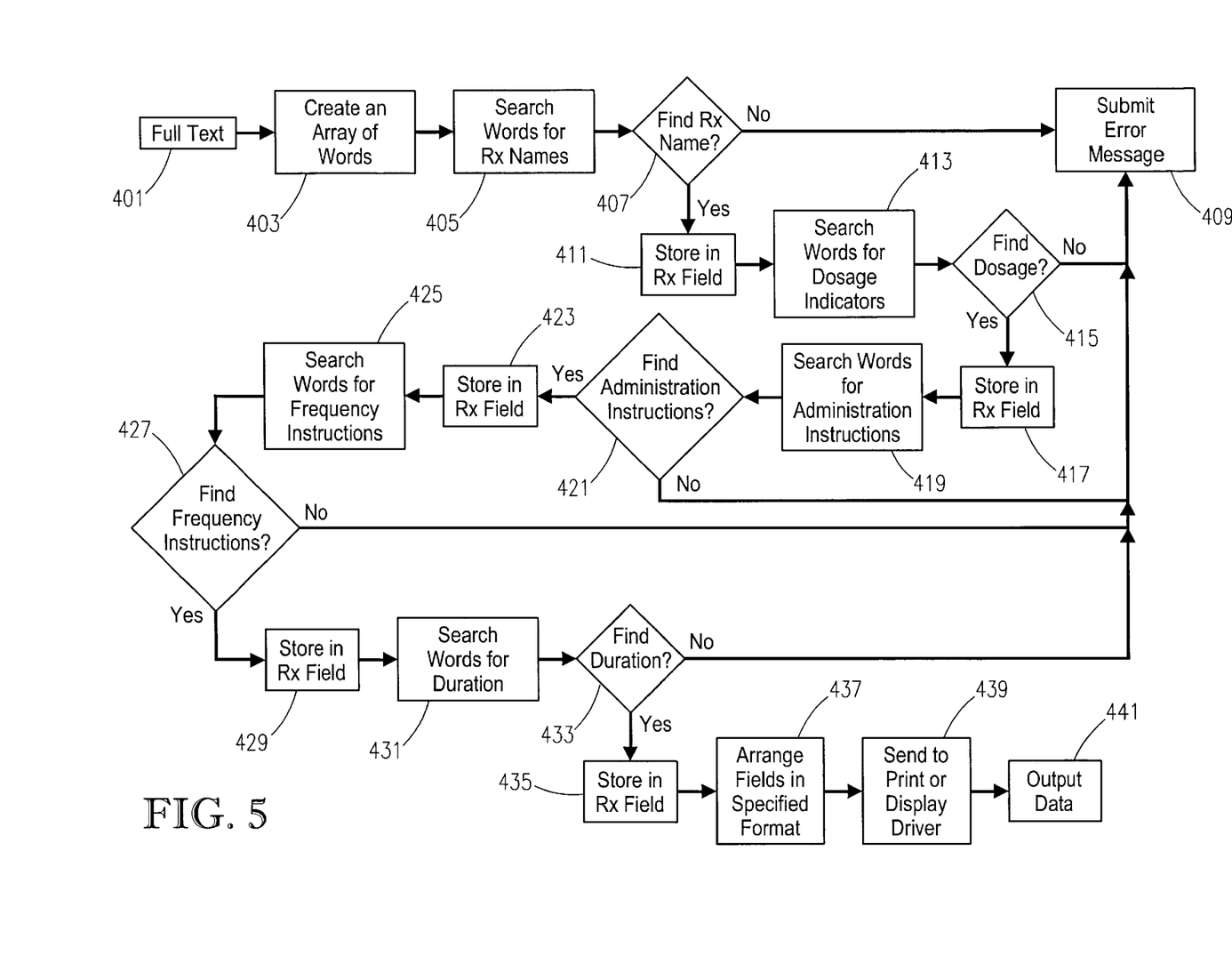
FIG. 5 is a software or firmware block diagram setting forth the flow functions of the prescription formatting and printing program.

The software flow functions of the prescription formatting module 40 for the preferred embodiment is schematically illustrated in FIG. 5. The full text as produced by the speech recognition software and represented schematically by the function block 200 in FIG. 5 is divided into an array of words as indicated by function block 202. First, the software searches the words for names of drugs as represented by function block 204. If no drug name is found, pursuant to function block 206, the software submits an error message represented by output block 208 and exits. When a drug name is identified, in function 206, the drug name is stored in a field identified as function block 210 in RAM 44. The software then continues to search through the array of words for words associated with dosage indicators as represented by function block 212. The software is preferably programmed to recognize the full range of anticipated phrases used to indicate dosage as represented by function block 214. These would primarily include weight of active medicament, e.g. mg., or meg., or measurements of volume, such as milliliters, teaspoons, etc., but might also include many other measurements. For some drugs, such as ointments, dosages might be more qualitative, and this would need to be included in the software. If no dosage data or equivalent is found, the software would again exit with an error message 208.

If terms for the prescribed dosage are found, these terms are stored in another field as represented by function block 216 in RAM 44. The software similarly may, if necessary, search for, find and store digital data representing words associated with drug administration, words associated with frequency of dosage, and terms associated with duration of the individual prescription, which are represented by the sequential function blocks 218, 220, 222, 224, 226, 228, 230, 232 and 234 of FIG. 5. When all of these terms are successfully identified, the five fields for (1) drug name, (2) dosage, (3) delivery instructions, (4) frequency, and (5) duration are assembled and formatted as indicated by function block 236, and sent to the print or display driver as represented by function block 238 which outputs appropriate digital data 240.

V. First Alternative Embodiment with Visual Display and Editing Capability

Figure 6:
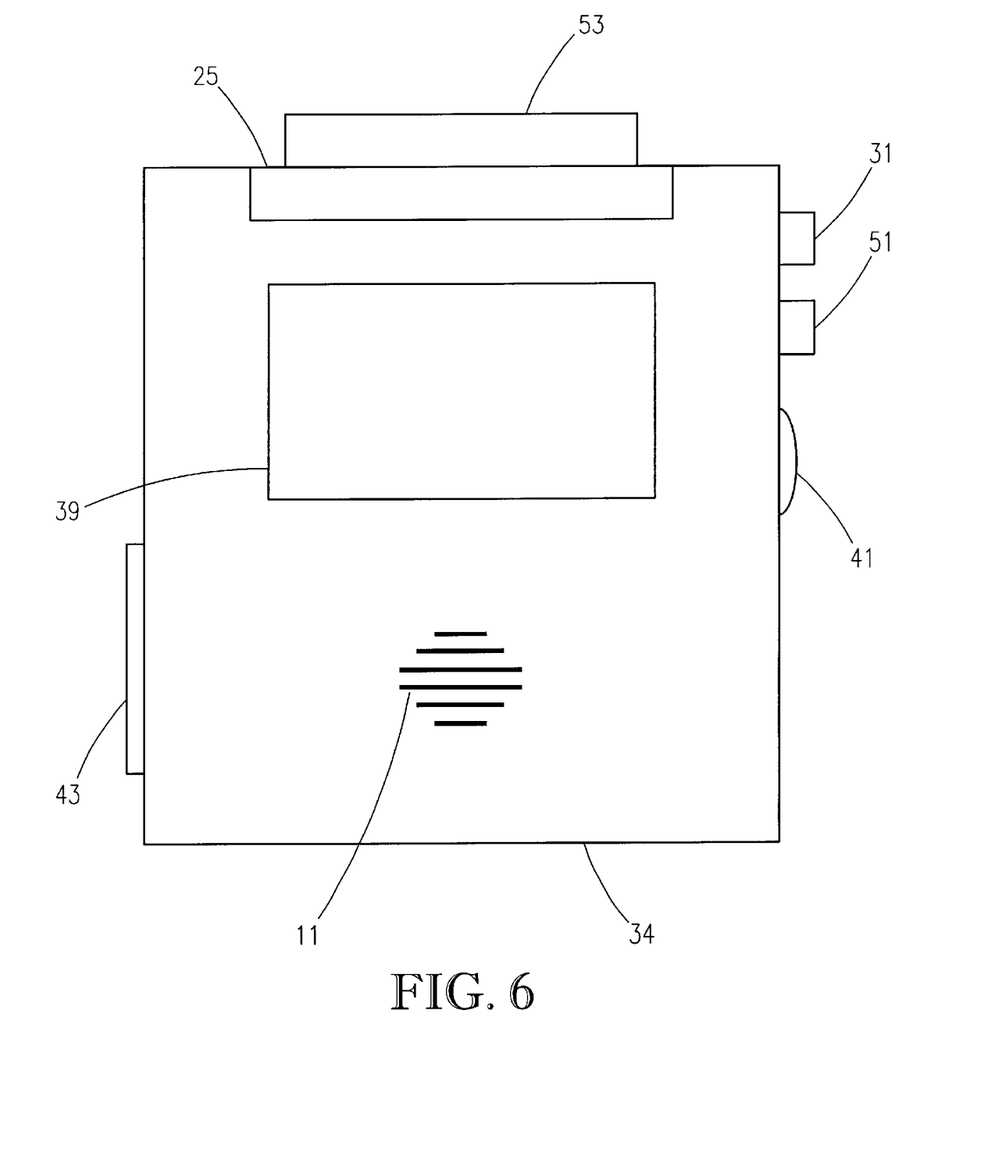
FIG. 6 depicts an external representation of the invention in an alternative embodiment, which includes a liquid crystal display as an additional output device, along with controls for modifying the prescription, and a long-term storage chip.

FIG. 6 is an external representation of in an alternative transcriber and printer unit 310, which adds to a video display the transcriber and printer unit 10 that allows a user to view the prescription and also provides a means for editing the prescription before printing. Externally, the only features of the transcriber and printer unit 310 visible to the user are the case 312, the microphone 314, the liquid crystal display (LCD) 360, the recording controller 318, a control 362 for editing the prescription, the print control 364, the Flash Memory Card 320, the printer 322, and the paper 324. Unit 310 remains simple to use while adding to the functionality of the unit.

Figure 7:
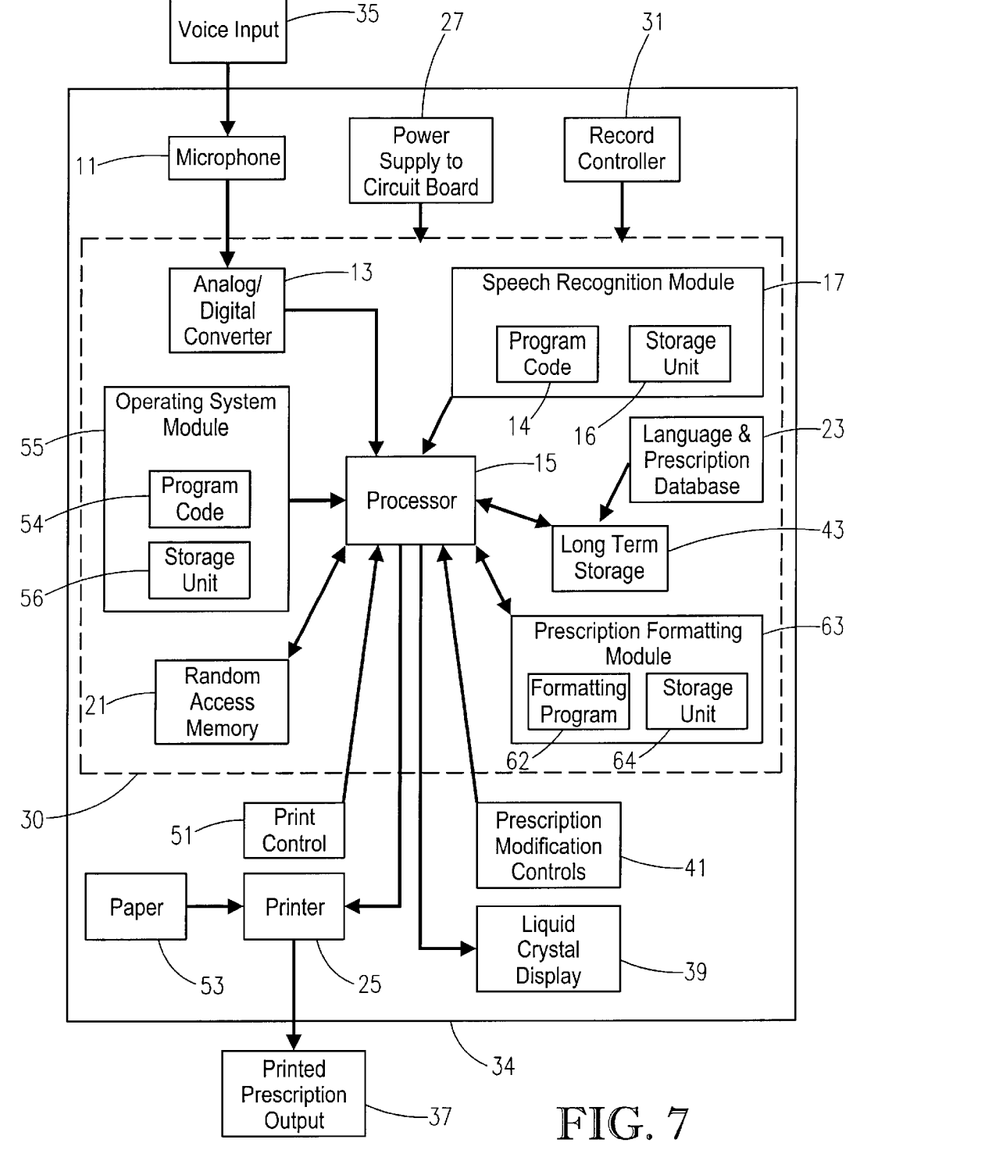
FIG. 7 is a simplified block diagram showing the components of an alternative embodiment of the invention, which includes a liquid crystal display as an additional output device, along with controls for modifying the prescription and a long-term storage chip.

FIG. 7 is a block diagram showing the internal set-up for the transcriber and printer unit 310. The internal components of unit 310 are identical to those of unit 10 as shown in FIG. 2, with the exception of components which provide for the display of the prescription information for visual observation by the physician prior to initiating printing of the prescription. There is no LED 16 in unit 310 in view of the provision of the LCD 360.

The edit control 362 and print control 364 are added components in unit 310. Furthermore, the operating system module 336 in unit 310 and the prescription formatting module 340 are different from their counterparts in unit 10.

The LCD 360 provides a convenient way for the user to verify that the results of the speech recognition analysis are correct. The LCD 360 visually displays the results of the software analysis of the physician's spoken words for verification of accuracy of the information before it is printed out by printer 322. The LCD 360 receives digital information directly from unit 310's CPU 34. The LCD 360 serves as a backup for the speech recognition software to permit confirmation of the accuracy of the speech recognition before printout of a prescription.

The LCD 360 of unit 310 may for example comprise an alphanumeric display available from Seiko Instruments. This type of LCD display is advantageous in that it is thin, lightweight, and requires low power. The display has a relatively wide viewing angle making the image displayed on the screen easy to view by the user of the unit.

The edit control dial 362 forming a part of unit 310 allows for selective modification of the speech recognition analysis after the user has viewed the results on the LCD display 360. After the user of unit 310 has spoken the words making up a prescription, at least the name of the drug will appear on the screen of the LCD. The physician can use the dial 362 on the side of case 312 to scroll through drugs in the database. If the drug name needs to be changed or corrected, this can quickly be done with control 362. The rotatable control 362 is operably connected to the CPU 34 and allows the processor 34 to display on the LCD 360 a choice of possible alternative drugs when the user requests that information. The language and prescription database software 42 generates this choice of words. The user can scroll down the list of alternative words and select the desired drug. The processor 34 can also display similar drugs or drug brand names when prompted by the user, giving the user access to other prescription and drug information that may aid in the accurate completion of the prescription. The user can then quickly correct any mistakes in the analysis and continue on with the printing of the prescription output indicated by function block 366 in FIG. 7. This procedure significantly decreases the possibility of mistakes in the printed output 366. The control 362 also offers the option to have the device continue on with the printing of the prescription. As can be seen in FIG. 7, the control 362 connects directly to the CPU 34, allowing the processor 34 to adjust the output on the LCD 360 accordingly. Again referring to FIG. 7, print control button 364 is required in unit 310 in order to control printing upon completion of the editing. This button preferably consists of a simple on/off switch.

Figure 8:
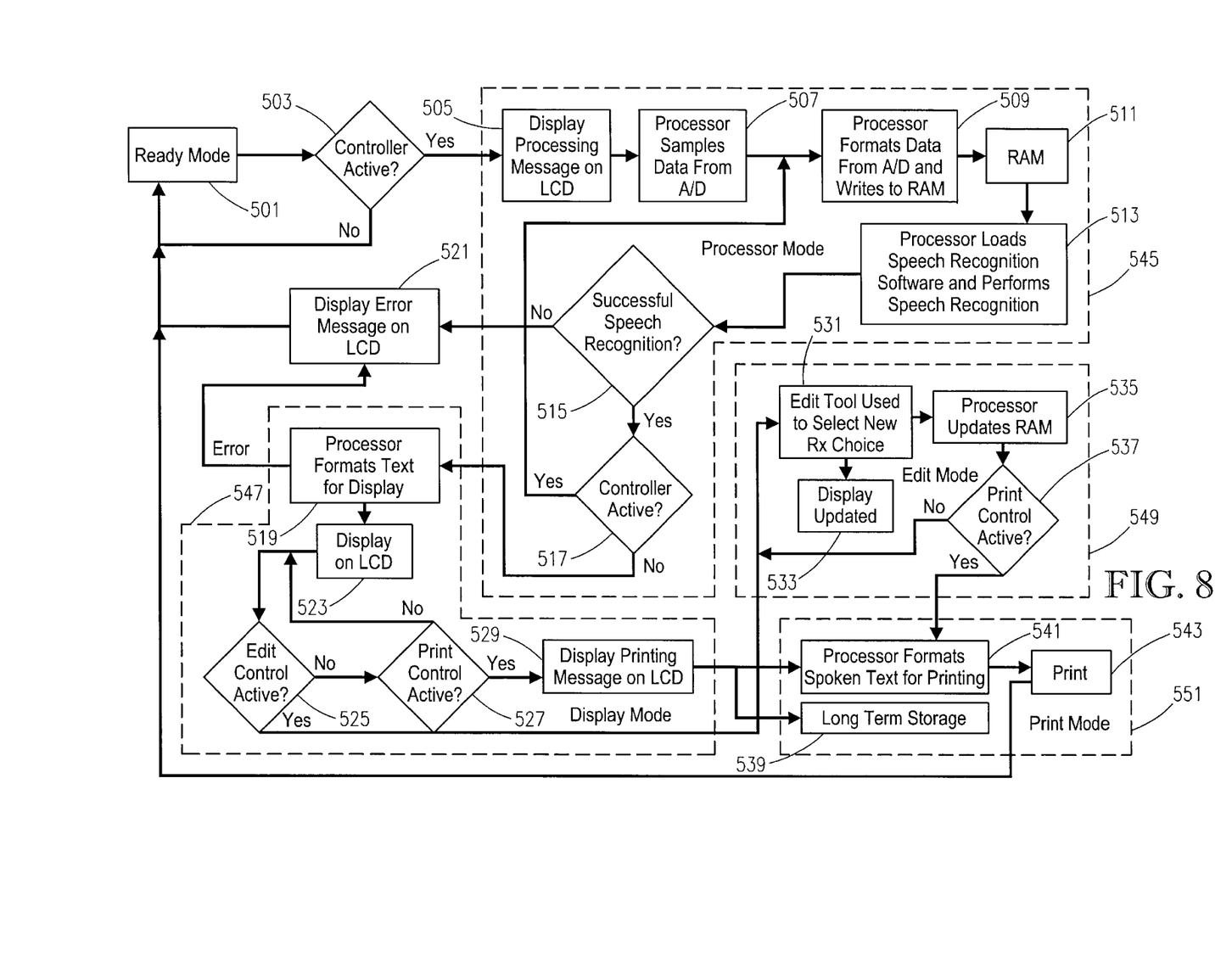
FIG. 8 is a software or firmware block diagram indicating central processor activity setting forth the flow function of the operating system for the device in the alternative embodiment shown in FIGS. 6 and 7.

FIG. 8 schematically represents the overall software flow functions of unit 310 which are implemented via the operating system module 336. In this alternative embodiment, the unit 310 has six operating modes represented by function blocks Ready Mode 400, Processor Mode 402, Error Mode 404, Display Mode 406, Edit Mode 408, and Print Mode 410. Ready Mode 400 and Processor Mode 402 function the same as Ready Mode 100 and Processor Mode 102 as previously described with respect to unit 10. The Error Mode represented by function block 404 replaces Standby Mode function block 104. In the event the speech recognition is not successful as represented by function block 412, the speech recognition software initiates an error message represented by function block 404 and an error message is displayed on the LCD 360. The unit 310 remains in Error Mode 404 until the user releases the record controller 318.

When the Processor Mode 402 successfully completes speech recognition function 412, the unit 310 moves into Display Mode function 406. The prescription formatting software formats the text for display in the same manner described and illustrated with respect to the flow diagram of FIG. 5. When the text has been successfully formatted for display as indicated by function block 414 of FIG. 8, the text is displayed in prescription format on the LCD 360 as indicated by function block 416. If customized prescription formats have previously been downloaded into the memory of unit 310, then the forms may be displayed on the LCD 360 as well.

After the text has been displayed as indicated by function block 416, the processor 34 continues to check the Edit Control 418 and Print Control 420 for activity. If the Edit Control function 418 is active, the unit moves to the Edit Mode function 408. If the print control 420 is active, the unit moves to Print Mode 410.

In Edit Mode 408, the physician uses the prescription edit control 362 if desired to scroll through the database of drug names as indicated by function block 422. The LCD 360 displays the drug name in a window indicated by function block 424 in FIG. 8. The window 424 may for example display the selected drug name as well as the two drugs which alphabetically appear just before and just after the selected drug. The selected drug would appear in the middle, highlighted. The physician may employ the Edit Control 362 to scroll up or down through the database of drugs indicated by function block 422. The drug appearing in the middle would always be highlighted, indicating that it is the selected drug. This Edit Mode 408 can be used by the physician to select another drug in the event that the speech recognition software mistakenly identified the wrong drug based upon the words spoken by the user. The Edit Control 362 sends a signal to the processor 34, which in turn updates the LCD 360 and updates the record stored in the RAM 444.

Once the desired drug is selected, whether Edit Mode function 408 is employed or not, the physician may then activate the Print Control function 420, thereby moving the device into the Print Mode function 410.

In Print Mode 410, the processor 34 formats the prescription data for printing as indicated by function block 426, including the use of any downloaded customized forms and submits the data to the print driver which in turns sends it to the printer represented by function block 428. Simultaneously, the processor 34 also writes the prescription record to long-term memory 430 for future reference.

VI. Second Alternative Embodiment with External Communications Capability

Figure 9:
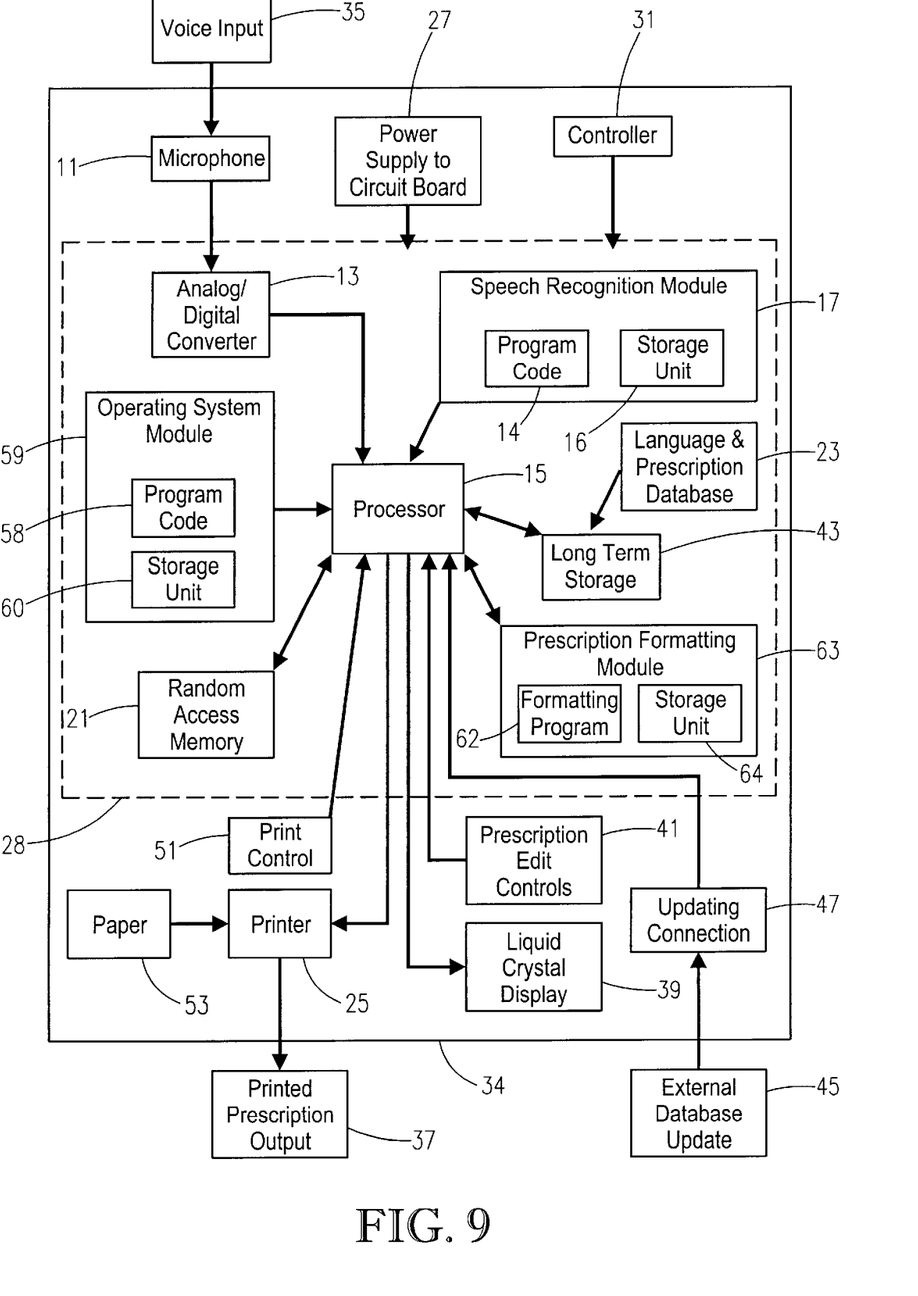
FIG. 9 is a simplified block diagram showing the components of a further embodiment of the invention, which includes a liquid crystal display as an additional output device, controls for modifying the prescription output, a long-term storage chip, and components permitting updating of the language and prescription database software from an external source.

FIG. 9 is the block diagram for another alternative embodiment of the transcribing and printing unit. This embodiment 510 provides for updating any of the software or data stored in long-term memory via an external update connection represented by function block 512. For practical implementation, the external update connection 510 preferably consists of an RS-232 serial connector which allows the user to connect the handheld medical prescription transcriber unit 510 to a personal computer. In this manner, download upgrades may be made to the speech recognition program module 38, the language and prescription database 42, the prescription formatting module 40, or the operating system module 36, and allow for uploading of prescription records stored in the long-term storage card 20. The connection can also be used to download preprinted electronic versions of forms into the memory for printing on every prescription, such as customized forms used by the user. Other than adding the external update connection, the only other difference between unit 310 and unit 510 is the change in the operating system modules. The operating system module 514 of unit 510 is the same as the operating system module 336 of unit 310, except that the operating system program code 516 of module 514 differs from the operating system program code 346 of unit 310 to allow the external communications.

The benefit of this external upgrading of the software programs and data stored in unit 510 is the fact that one would not have to remove the long-term storage device 20, such as a Flash Memory Card, and update this card using separate hardware attached to a personal computer, in order to update the database 42, or any of the programs 46, 50 and 54, therefore significantly simplifying this necessary process. It would allow for more frequent updating of the database 42 because of the ease with which this process can be done. Furthermore, provision for external upgrading of programs and the database reduces the overall cost of the device because the removable Flash Memory Card could be replaced with a less expensive internal Electrically Erasable Programmable Read Only Memory (EEPROM). The EEPROM would not require removal from the transcriber in order to update its contents. EEPROMs are available in a wide variety of capacities from a variety of vendors. This updating capability may be deemed necessary due to the frequent development and use of new drugs and drug brands. Unit 510 operates in the same manner as previously described in connection with unit 310.

What is claimed is:

1. A hand held unitary medical prescription transcriber and printer unit comprising:

structure of a size to be conveniently held in a user's band, said structure including,
a voice responsive input device which converts the user's spoken word acoustic inputs into analog signals,
a converter operable to convert said analog signals into corresponding outputted digital signals,
a database of medical prescription information stored in digital format,
a formatting module operable to match only outputted digital signals from the converter with corresponding prescription digital data stored in the database to automatically format the matched digital signals into a form representative of a medical prescription, and
an integral printer operable to receive the formatted digital signals and to print out the formatted digital signals as readable hard copy directly from the unit.

2. A hand held medical transcriber and printer unit as set forth in claim 1, wherein said voice responsive device includes a microphone.

3. A hand held medical transcriber and printer unit as set forth in claim 1, wherein said voice responsive device is voice activated.

4. A hand held medical transcriber and printer unit as set forth in claim 1, wherein as provided an on off switch controlling operation of the voice responsive device.

5. A hand held medical transcriber and printer unit as set forth in claim 1, wherein is provided a storage element for the database information, said element being removably mounted in said structure for periodic updating of the database.

6. A hand held medical transcriber and printer unit as set forth in claim 1, wherein is provided code segments which generate an error message observable by the user of the unit in the event the formatting module is unable to match outputted digital signals from the converter with corresponding digital data stored in the database.

7. A hand held medical transcriber and printer unit as set forth in claim 1, wherein is provided a programmable read-only memory module containing code segments coordinating operation of the voice responsive input device, the converter, the formatting module, and the printer.

8. A hand held medical transcriber and printer unit as set forth in claim 1, wherein is included random access memory for temporary storage of the outputted digital signals and the formatted digital signals.

9. A hand held medical transcriber and printer unit as set forth in claim 1, wherein said printer is a thermal printer.

10. A hand held medical transcriber and printer unit as set forth in claim 1, wherein is included a recorder for recording each prescription which is transcribed and printed out by the unit permitting downloading thereof to a remote site and/or to provide a history of prescriptions written over a predetermined period of time.

11. A hand held medical transcriber and printer unit as set forth in claim 1, wherein is provided a display screen operable to display the formatted digital signals in readable word form prior to printing thereof.

12. A hand held medical transcriber and printer unit as set forth in claim 11, wherein is provided edit code segments permitting the user of the hand held unit to change the formatted digital signals after viewing the readout thereof on the display screen.

13. A hand held medical transcriber and printer unit as set forth in claim 11, wherein is provided alternate prescription information code segments operable to display a selection of prescription information on said screen different from but related to the formatted digital signals, and for permitting the user of the hand held unit to select different prescription information for delivery to the printer.

14. A hand held medical transcriber and printer unit as set forth in claim 1, wherein is provided an input connected to the database for selective modification of the database.

15. A process for preparing a printed copy of a medical prescription using a hand held transcriber and printer unit, said process comprising:

providing a voice responsive input device which converts the user's spoken word acoustic inputs into analog signals;
converting said analog signals into corresponding digital signals;
providing a database of medical prescription information stored in digital format;
matching only the digital signals with corresponding digital data stored in the database to automatically format the matched digital data into a form representative of a medical prescription; and
printing out a readable hard copy of the prescription information directly from the unit.

16. A process for preparing a printed copy of a medical prescription using a hand held transcriber and printer unit as set forth in claim 15, wherein is provided the step of recording a history of prescriptions transcribed and printed by the unit for periodic review and recordkeeping purposes.

17. A process for preparing a printed copy of a medical prescription using a hand held transcriber and printer unit as set forth in claim 15, wherein is provided the step of transferring the recorded history of prescriptions transcribed and printed by the unit to a remote storage site.

18. A process for preparing a printed copy of a medical prescription using a hand held transcriber and printer unit as set forth in claim 15, wherein is included the step of providing a voice activated acoustic input device.

19. A process for preparing a printed copy of a medical prescription using a hand held transcriber and printer unit as set forth in claim 15, wherein is included the step of periodically introducing additional digital data into the database to update the medical information database.

20. A process for preparing a printed copy of medical prescription using a hand held transcriber and printer unit as set forth in claim 15, wherein is included the step of providing a display screen which is operable to display the prescription information in readable word form prior to printing thereof.

21. A process for preparing aprinted copy of a medical prescription using a hand held transcriber and printer unit as set forth in claim 20, wherein is included the step of displaying the prescription information on the display screen to permit the user of the hand held transcriber and printer to edit the prescription information prior to printing of hard copy thereof.

22. A process for preparing a printed copy of a medical prescription using a hand held transcriber and printer unit as set forth in claim 20, wherein is included the step of providing a display of alternate medical information on the display screen, and permitting the user to select particular medical information from that displayed on the display screen.

23. A process for preparing a printed copy of a medical prescription using a hand held transcriber and printer unit as set forth in claim 20, wherein is provided the step of displaying an error message on the display screen in the event a match is not made between the digital signals and the prescription information digital data stored in the database.

24. A process for preparing a printed copy of a medical prescription using a held transcriber and printer unit as set forth in claim 15, which includes the step of spectrally analyzing the digital signals by repetitively sampling thereof to facilitate matching of the spectrally analyzed digital signals with corresponding digital data in the database.

25. A hand held unitary medical prescription transcriber and printer unit comprising:
   a voice responsive input device which coverts a user's spoken word acoustic inputs into analog signals;
   a converter operable to convert the analog signals into corresponding outputted digital signals;
   a formatting module operable to automatically format thin outputted digital signals into a form representative of a prescription by searching the outputted digital signals to identify prescription information; and
   an integral printer operable to print out the formatted digital signals as readable hard copy directly from the unit.

26. The handheld medical transcriber as set forth in claim 25, wherein the prescription information includes a prescription name, a prescription dosage, and a prescription duration.

27. The handheld medical transcriber as set forth in claim 25, wherein the unit includes a database of medical prescription information stored in digital format.

28. The handheld medical transcriber as set forth in claim 27, wherein the formatting module identifies the prescription information by matching the outputted digital signals with the medical prescription information stored in the database.

29. The handheld medical transcriber as set forth in claim 27, wherein the formatting module searches the database of medical prescription information for information associated with the formatted digital signals.

* * * * *